United States Patent

Matthews et al.

[11] Patent Number: 5,856,500
[45] Date of Patent: Jan. 5, 1999

[54] SYNTHESIS OF THIAZOLE DERIVATIVES

[75] Inventors: Michael D. Matthews, Walker; Arcelio J. Malcolm, Baton Rouge, both of La.

[73] Assignee: Albemarle Corporation, Richmond, Va.

[21] Appl. No.: 816,112

[22] Filed: Mar. 11, 1997

[51] Int. Cl.$^6$ .................................................. C07D 277/18
[52] U.S. Cl. .......................................... 548/184; 548/193
[58] Field of Search ...................................... 548/184, 193

[56] References Cited

U.S. PATENT DOCUMENTS

| | | | |
|---|---|---|---|
| 4,262,126 | 4/1981 | Gilman et al. | 548/193 |
| 4,283,408 | 8/1981 | Hirata et al. | 424/270 |
| 4,347,370 | 8/1982 | Gilman et al. | 548/193 |
| 4,496,737 | 1/1985 | Hoffman, Jr. | 548/193 |
| 4,562,261 | 12/1985 | Hirata et al. | 548/184 |
| 4,609,737 | 9/1986 | Hirata et al. | 548/184 |
| 4,835,281 | 5/1989 | Bod et al. | 548/197 |

FOREIGN PATENT DOCUMENTS

| | | |
|---|---|---|
| 0389510 | 12/1989 | Austria . |
| 0087274 | 8/1983 | European Pat. Off. . |
| 0284536 | 9/1988 | European Pat. Off. . |
| 0322335 | 6/1989 | European Pat. Off. . |
| 0356366 | 2/1990 | European Pat. Off. . |
| 2007375 | 6/1989 | Spain . |
| 2220415 | 12/1991 | United Kingdom . |

*Primary Examiner*—Johann Richter
*Assistant Examiner*—Ebenezer Sackey
*Attorney, Agent, or Firm*—Philip M. Pippenger

[57] ABSTRACT

N-[4-(Cyanoethylthiomethyl)-2-thiazolyl]guanidine, is prepared by (a) mixing 1,3-dihaloacetone and 2-imino-4-thiobiuret in a suitable polar organic solvent at initial temperatures of about −10° to about 25° C., and agitating the mixture at about −10° to about 60° C. for at least about 1 hour; (b) heating the resultant mixture at about 40° to about 60° C. for at least about 0.5 hour; (c) mixing with the mixture from (b), thiourea and then water at about 40° to about 60° C. for a period of at least about 1 hour; (d) removing liquid polar solvent from the mixture of (c); and (e) mixing with the mixture from (d), 3-halopropionitrile and water-soluble alcohol, ether, or ether-alcohol, followed by aqueous alkali metal hydroxide while maintaining the temperature at below about 20° C., to form N-[4-(cyanoethylthiomethyl)-2-thiazolyl]guanidine. The process avoids isolating and purifying any of the intermediates, and can be conducted in the same vessel, as a "one-pot" synthesis.

20 Claims, No Drawings

SYNTHESIS OF THIAZOLE DERIVATIVES

TECHNICAL FIELD

This invention relates to a novel synthesis procedure for the efficient production of a key intermediate useful in the preparation of the pharmaceutical, famotidine.

BACKGROUND

Famotidine is a well-known histamine H2-receptor antagonist and gastric acid secretion inhibitor. A key intermediate for the preparation of this compound is N-[4-(cyanoethylthiomethyl)-2-thiazolyl]guanidine (also known as N-[4-[[(2-cyanoethyl)-thio]methyl]-2-thiazoyl]guanidine). To prepare this intermediate U.S. Pat. Nos. 4,562,261 and 4,609,737 describe a route based on N-[4-(chloromethyl)-4,5-dihydro-4-hydroxy-2-thiazolyl]-guanidine hydrochloride as the starting material. The synthesis involves preparing this starting material by portionwise addition of (aminoiminomethyl)thiourea to dichloroacetone in acetone at temperatures of about −5° to −7° C. and stirring the resultant mixture for 5 days at below 0° C. The resultant N-[4-(chloromethyl)-4,5-dihydro-4-hydroxy-2-thiazolyl]-guanidine hydrochloride is isolated, purified and converted to N-[4-[[(2-aminoiminomethyl)thio]methyl]-2-thiazoyl]guanidine) dihydrochloride by reaction with thiourea. Without isolating this intermediate, the reaction mixture is cooled below 10° C. and to the solution are added 3-chloropropionitrile and isopropyl alcohol, followed by dropwise addition of aqueous NaOH whereby crystals of N-[4-(cyanoethylthiomethyl)-2-thiazolyl]guanidine are formed.

SUMMARY OF THE INVENTION

This invention provides a process which produces N-[4-(cyanoethylthiomethyl)-2-thiazolyl]guanidine by a sequence of reactions conducted under moderate reaction conditions and without need for isolation or purification of any intermediate formed in the process. And since use of prolonged reaction periods at extremely low temperatures is unnecessary, the economics of the operation are significantly improved.

Thus pursuant to this invention there is provided a process for the preparation of N-[4-(cyanoethylthiomethyl)-2-thiazolyl]guanidine, which process comprises:

a) mixing 1,3-dihaloacetone and 2-imino-4-thiobiuret in a suitable chemically indifferent reaction medium comprising one or more liquid polar solvents such as ketones, alcohols, ethers, ether-alcohols or mixtures of any two or more of such solvents at one or more initial temperatures in the range of about −10° to about 25° C., and agitating the mixture at one or more temperatures in the range of about −10° to about 60° C. for a period of at least about 1 hour;

b) heating the resultant mixture at one or more temperatures in the range of about 40° to about 60° C. for a period of at least about 0.5 hour;

c) mixing with mixture from b) thiourea and then water at one or more temperatures in the range of about 40° to about 60° C. for a period of at least about 1 hour;

d) removing liquid polar solvent from the mixture of c); and e) mixing with mixture from d), 3-halopropionitrile and at least one water-soluble alcohol, ether and/or ether-alcohol, followed by aqueous alkali metal hydroxide while maintaining the temperature at below about 15° C., to form N-[4-(cyanoethylthiomethyl)-2-thiazolyl] guanidine.

Other embodiments and features of the invention will be still further apparent from the ensuing description and appended claims.

FURTHER DETAILED DESCRIPTION

N-[4-(cyanoethylthiomethyl)-2-thiazolyl]guanidine can be represented by the formula:

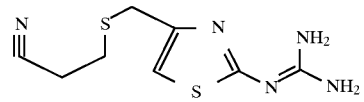

It will be appreciated that the guanidine moiety is capable of undergoing tautomerization to a terminal —NH—C(—NH$_2$) (=NH) moiety.

Although the other 1,3-dihaloacetones can be used as the starting material in the process, 1,3-dichloroacetone is a suitable reactant, if proper conditions and safeguards are used in handling the material. The preferred reactant, however, is 1,3-dibromoacetone.

Polar solvents that can be used in a) above include hydrocarbyl ketones (e.g., acetone, methyl ethyl ketone, 2-pentanone, 3-pentanone, 2-hexanone, 3-hexanone, cyclohexanone, and the like), alcohols (e.g., ethanol, 1-propanol, 2-propanol, 1-butanol, 2-methyl-1-propanol, and the like,), ethers (e.g., 1,2-dimethoxyethane, dipropyl ether, diisopropyl ether, tetrahydrofuran, and the like) and ether-alcohols (e.g., ethylene glycol monomethyl ether, tetrahydrofurfuryl alcohol, and the like). Mixtures of one or more ketones and/or one or more alcohols and/or one or more ethers and/or one or more ether-alcohols can be used, if desired. Preferably, the solvent or mixture of solvents is one that at ordinary atmospheric pressure is a liquid over the range of −15° C. to 65° C. and that boils at one or more temperatures below about 90° C. at 760 mm Hg pressure, as this facilitates their removal in d) above after they have served their purpose in a), b) and c) above.

Proportions of the reactants used in a) will typically be from about 1 to about 1.1 moles of 2-imino-4-thiobiuret per mole of the 1,3-dihaloacetone.

On mixing the reactants in a) an exothermic reaction occurs. Thus to assist is temperature control, it is desirable to pre-cool at least the polar solvent (which may contain either reactant, preferably the 1,3-dihaloacetone) to a temperature in the range of about 0° to about 10° C. before initiating the feed of the two reactants, or the feed of the second reactant to be fed. Upon initiation of the reaction, the exotherm will heat up the reaction mixture to desirable or at least readily controllable temperatures. The reaction mixture should be agitated as by use of a mechanical stirrer to ensure thorough mixing of the reactants within the reaction mixture.

The period in a) during which the mixture formed in a) is kept in the range of about −10° to about 60° C. with agitation typically falls in the range of about 1 to about 48 hours, and preferably is in the range of about 1 to about 8 hours.

In b), the period during which the reaction mixture is heated at one or more temperatures in the range of about 40° to about 60° C. typically falls in the range of about 0.5 to about 2 hours, but longer periods of time do no harm other than to increase overall production time. Preferred temperatures for this operation are in the range of about 45° to about 55° C., and most preferably about 50° C. It is desirable to continuously agitate the mixture during this operation, although again, periods of quiescence do no material harm.

The desired intermediate product in the reaction mixture from b) is N-(4-halomethyl-2-thiazolyl)guanidine or the guanidine tautomer thereof. Thus when 1,3-dibromoacetone is used as the starting material, the product is N-(4-bromomethyl-2-thiazolyl)guanidine (or tautomer thereof) which normally is present as the hydrobromide salt, which may be depicted by the formula:

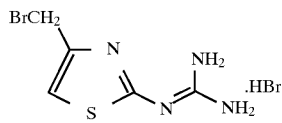

In c) above, the thiourea is preferably added to the reaction mixture while agitating the mixture. The amount of thiourea used is about 1 to about 1.1 moles per mole of 1,3-dihaloacetone charged in a). The amount of water added to the reaction mixture should be equal to about 50 to about 200% of the mass of the 1,3-dihaloacetone charged in a). If desired, the thiourea and water can be concurrently added to the reaction mixture, for example as a solution or slurry. Preferably however, the water is added after the thiourea has been added. The period of time the resultant mixture is agitated at about 40° to about 60° C. is typically about 1 hour but depending upon the scale of operation, longer periods can be used if desired.

Removal of polar solvent in d) is best effected by conducting a vacuum distillation, which, depending on the solvent(s) employed, typically involves temperatures in the range of about 40° to about 50° C. and pressures in the range of about 50 to about 300 mm of Hg. The solvent removed from the reaction mixture in this operation can be recycled for use in a).

The amount of 3-halopropionitrile mixed with (preferably added to) the residual mixture from d) is generally in the range of about 1 to about 1.2 moles per mole of 1,3-dihaloacetone used in a) above. The water-soluble alcohol and/or ether and/or ether-alcohol used in e) serves as a compatible medium or at least a substantially compatible medium in which the 3-halopropionitrile and the aqueous alkali metal hydroxide solution can interact with each other more readily than if they were in a completely heterogeneous mixture. Thus the one or more alcohols and/or ethers and/or ether-alcohols used need not be completely miscible with water. Instead, they should be capable of dissolving to the extent of at least about 20 grams per 100 mL of water at 25° C., and in general, the higher their water solubility, the better. A few examples of suitable alcohols include, methanol, ethanol, 1-propanol, 2-propanol, ethylene glycol, and mixtures of two or more of the foregoing. A few examples of suitable ethers include tetrahydrofuran, 1,3-dioxolane, 2-methyl-1,3-dioxolane, 1,4-dioxane, and mixtures of two or more of the foregoing. A few examples of suitable ether-alcohols include ethylene glycol monomethyl ether, ethylene glycol monoethyl ether, ethylene glycol monobutyl ether, tetrahydrofurfuryl alcohol, and mixture of two or more of the foregoing. Mixtures of one or more water-soluble alcohols with one or more water-soluble ethers or with one or more water-soluble ether-alcohols can also be used. Similarly, mixtures of one or more water-soluble ethers with one or more water-soluble ether-alcohols, and mixtures of one or more water-soluble alcohols with one or more water-soluble ethers and with one or more water-soluble ether-alcohols can also be used. Use of 2-propanol as the compatibilizing solvent is preferred. Amounts of such water-soluble alcohols, ethers and/or ether-alcohols used in e) above are typically in the range of about 2 to about 4 times the mass of the 3-chloropropionitrile used in e). These materials can be added concurrently or sequentially, but preferably the 3-halopropionitrile is added before the water-soluble alcohol, ether and/or ether-alcohol. While 3-chloropropionitrile is preferred for use in this reaction because of its availability, suitable reactivity and relatively low cost, other 3-halopropionitriles, such as 3-bromopropionitrile can be used either individually or together with 3-chloropropionitrile.

If a water-soluble alcohol, ether and/or ether-alcohol was employed as the solvent in a), it can be recovered in d) and used in e).

While an aqueous solution of any alkali metal hydroxide can be used in e), sodium hydroxide and potassium hydroxide are preferred because of their cost and availability, sodium hydroxide being most preferred. The solution can be formed by dissolving the oxides and/or hydroxide of the alkali metal in water. The alkali metal hydroxide in the resultant solution is of course in ionized form as alkali metal cations and hydroxyl anions. To facilitate recovery of the N-[4-(cyanoethylthiomethyl)-2-thiazolyl]guanidine from the resultant mixture, it is desirable, though not essential, to seed the mixture with crystals of N-[4-(cyanoethylthiomethyl)-2-thiazolyl]guanidine to promote formation of the product as a precipitate which can be readily recovered by conventional separation techniques such as filtration, centrifugation, decantation, or the like. Filtration followed by washing the product with cool (e.g., 1° to 15° C.) water is a preferred procedure.

Among the advantages of this invention is that it is unnecessary to perform the initial reaction at temperatures of 0° C. and below. Moreover, the reaction is relatively rapid under the conditions used in a) and b) above. In addition the overall process, when properly performed, thus far has been found capable of producing the N-[4-(cyanoethylthiomethyl)-2-thiazolyl]guanidine in yields as high as 59% based on the 1,3-haloacetone used. Product of purities as high as 88% have been achieved in the practice of the process of this invention. Other advantages of the process are improved process economics, decreased process cycle time, reduced reaction equipment requirements, simpler process operations, improved opportunity for recycle of raw materials, and formation of less chemical waste.

Still another advantage when using 1,3-dibromoacetone in a) above is that the 1,3-dibromoacetone need not be of high purity. Indeed, the 1,3-dibromoacetone can contain significant amounts of monobromacetone and 1,1,3-tribromoacetone without these analogous compounds participating to any significant extent in the overall reaction. This in turn has a favorable effect upon raw material costs and process economics. Accordingly, the 1,3-dibromoacetone used in the process can contain monobromoacetone or 1,1,3-tribromoacetone, or both, in an amount of up to 0.3 mole per mole 1,3-dibromoacetone.

It will be understood that those proportions given above which are based on the amount of 1,3-haloacetone used in a) presuppose that each reaction mixture is used in toto in the ensuing operation of the above sequence and that each reaction is allowed to proceed at least substantially to completion. If only a portion of a given reaction mixture is being used in the ensuing step, then the specified amounts relating back to the amount of the 1,3-dihaloacetone should be proportionately reduced in all ensuing steps.

It will be seen that the process of this invention is conducted without isolating and purifying any of the intermediates. If desired, the process sequence can be conducted in two or more vessels connected in series, such as by transferring the entire reaction mixture from c) above to another vessel in which the operation of d) above is conducted, and then transferring the residual reaction product from d) to another vessel in which e) above is carried out. In a preferred embodiment, all of the steps a) through e) inclusive are conducted in the same appropriately-equipped reaction vessel, as a so-called "one-pot" synthesis.

The following example illustrates the practice and advantages of this invention, and is not to be construed as constituting any limitation on the scope of the invention.

EXAMPLE

Into a 500 mL round bottom flask equipped with an overhead stirrer and under an inert atmosphere was added 25 g of 1,3-dichloroacetone (0.197 mol) and 75 g of acetone. The reaction mixture was cooled to 10° C. and 23.2 g 2-imino-4-thiobiuret (0.197 mol) was added. The reaction mixture was stirred for one hour at 10 C. The reaction mixture was then heated to 40° C. and 15 g of thiourea (0.197 mol) was added, followed by the addition of 100 g of water. The mixture was heated to and held at 52° C. for one hour. Acetone was then removed by vacuum distillation. To the reaction mixture was added 100 g of water, 17 g of 3-chloropropionitrile (0.190 mol) and 40 g of isopropyl alcohol. The reaction mixture was cooled below 10° C. and 25 g of an aqueous solution of sodium hydroxide (80 g water) was added dropwise maintaining the reaction temperature below 10° C. The reaction mixture was for 2 hours, filtered and washed to produce 28 g of N-[4-(cyanoethylthiomethyl)-2-thiazolyl]guanidine product.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. In short, the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

The structural formulas presented herein are for the purpose of illustrating the molecular makeup of the compounds depicted. However, such formulas do not represent geometric or spatial configurations or isomeric forms of the compounds.

By "chemically indifferent" is meant that the medium enables the desired reaction(s) to proceed. The medium may be truly inert such that it does not complex with or otherwise alter the composition of either of the reactants, or it may be innocuous in the sense that whatever takes place between the solvent(s) and the reactant(s) (e.g., solvation, complex formation, or etc.) the desired reaction takes place. In short, the medium does not prevent or materially interfere with the occurrence of the desired reaction leading to the desired product.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for the preparation of N-[4-(cyanoethylthiomethyl)-2-thiazolyl]guanidine, which process comprises:

a) mixing 1,3-dihaloacetone and 2-imino-4-thiobiuret in a chemically indifferent reaction medium comprising at least one polar organic solvent at one or more initial temperatures in the range of about −10° to about 25° C., and agitating the mixture at one or more temperatures in the range of about −10° to about 60° C. for a period of at least about 1 hour;

b) heating the resultant mixture at one or more temperatures in the range of about 40° to about 60° C. for a period of at least about 0.5 hour;

c) mixing with the mixture from b), thiourea and then water at one or more temperatures in the range of about 40° to about 60° C. for a period of at least about 1 hour;

d) removing liquid polar solvent from the mixture of c); and e) mixing with the mixture from d), 3-halopropionitrile and at least one water-soluble alcohol, ether, or ether-alcohol, or a mixture of any two or more of them, followed by aqueous alkali metal hydroxide while maintaining the temperature at below about 20° C., to form N-[4-(cyanoethylthiomethyl)-2-thiazolyl]guanidine.

2. A process according to claim 1 wherein the 1,3-dihaloacetone used is 1,3-dibromoacetone.

3. A process according to claim 1 wherein the 1,3-dihaloacetone used is 1,3-dichloroacetone.

4. A process according to claim 1 wherein the reaction medium of a) comprises one or more polar solvents selected from hydrocarbyl ketones, alcohols, ethers and ether-alcohols that are in the liquid state at the temperatures employed.

5. A process according to claim 1 wherein the amount of 2-imino-4-thiobiuret used in a) is about 1 to about 1.1 moles per mole of 1,3-dihaloacetone.

6. A process according to claim 1 wherein in conducting a) at least the reaction medium is pre-cooled to a temperature in the range of about 0° to about 10° C. before initiating the mixing of 1,3-dihaloacetone and 2-imino-4-thiobiuret therein.

7. A process according to claim 1 wherein in a) the 2-imino4-thiobiuret is fed into a pre-cooled mixture formed from (i) the 1,3-dihaloacetone and (ii) the reaction medium, and wherein the temperature of said pre-cooled mixture is initially in the range of about 0° to about 10° C.

8. A process according to claim 1 wherein in a) the 1,3-dihaloacetone is fed into a pre-cooled mixture formed from (i) the 2-imino-4-thiobiuret and (ii) the reaction medium, and wherein the temperature of said pre-cooled mixture is initially in the range of about 0° to about 10° C.

9. A process according to claim 1 wherein in d) the liquid polar solvent is removed from the mixture of c) by reduced pressure distillation.

10. A process according to claim 1 wherein in e) the amount of 3-halopropionitrile used is in the range of about 1 to about 1.2 moles per mole of 1,3-dihaloacetone used in a).

11. A process according to claim 1 wherein the 3-halopropionitrile used is 3-chloropropionitrile.

12. A process according to claim 1 wherein the 3-halopropionitrile used is 3-bromopropionitrile.

13. A process according to claim 1 wherein a), b), c), d), and e) are conducted without isolating and purifying any of the intermediates formed in the process.

14. A process according to claim 1 wherein a), b), c), d), and e) are conducted in the same reaction vessel.

15. A process according to claim 1 wherein a), b), c), d), and e) are conducted without isolating and purifying any of the intermediates formed in the process, and wherein a), b), c), d), and e) are conducted in the same reaction vessel.

16. A process according to claim 1 wherein:
1) the 1,3-dihaloacetone used is 1,3-dibromoacetone or 1,3-dichloroacetone;
2) the reaction medium of a) comprises one or more polar solvents selected from hydrocarbyl ketones, alcohols, ethers and ether-alcohols that are in the liquid state at the temperatures employed;
3) the 2-imino-4-thiobiuret is fed into a pre-cooled mixture formed from (i) the 1,3-dihaloacetone and (ii) the reaction medium, and wherein the temperature of said pre-cooled mixture is initially in the range of about 0° to about 10° C.;
4) in d) the liquid polar solvent is removed from the mixture of c) by reduced pressure distillation; and
5) the 3-halopropionitrile used is 3-chloropropionitrile.

17. A process according to claim 16 wherein the polar solvent or mixture of solvents of a) at ordinary atmospheric pressure is a liquid over the range of −15° C. to 65° C. and boils at one or more temperatures below about 90° C. at 760 mm Hg pressure.

18. A process according to claim 16 wherein the amount of 2-imino-4-thiobiuret used in a) is about 1 to about 1.1 moles per mole of the 1,3-dihaloacetone, and wherein the amount of the 3-halopropionitrile used in e) is in the range of about 1 to about 1.2 moles per mole of the 1,3-dihaloacetone used in a).

19. A process according to claim 18 wherein the polar solvent or mixture of solvents of a) at ordinary atmospheric pressure is a liquid over the range of −15° C. to 65° C. and boils at one or more temperatures below about 90° C. at 760 mm Hg pressure.

20. A process according to claim 19 wherein a), b), c), d), and e) are conducted in the same reaction vessel.

* * * * *